United States Patent [19]

Castro

[11] Patent Number: 5,356,421

[45] Date of Patent: Oct. 18, 1994

[54] SAFETY TROCAR WITH LOCKING HANDLES

[75] Inventor: Salvatore Castro, Seymour, Conn.

[73] Assignee: United States Surgical Corporation, Norwalk, Conn.

[21] Appl. No.: 957,673

[22] Filed: Oct. 7, 1992

[51] Int. Cl.⁵ ............................................. A61M 5/18
[52] U.S. Cl. ..................................... 606/185; 604/164
[58] Field of Search ............... 604/160, 161, 164, 165, 604/168, 169, 185, 188, 246–248, 264, 272, 274, 110, 51, 283; 606/184, 185; 128/751–754; 30/151, 152, 162, 366–368

[56] References Cited

U.S. PATENT DOCUMENTS

| | | |
|---|---|---|
| 1,213,001 | 1/1917 | Philips . |
| 2,256,942 | 9/1941 | Duffy . |
| 2,496,111 | 9/1947 | Turkel . |
| 2,623,521 | 12/1952 | Shaw . |
| 3,030,959 | 4/1962 | Grünert . |
| 3,039,468 | 6/1962 | Price . |
| 3,605,744 | 9/1971 | Dwyer . |
| 3,643,649 | 2/1972 | Amato . |
| 3,657,812 | 4/1972 | Lee . |
| 3,713,447 | 1/1973 | Adair . |
| 3,817,251 | 6/1974 | Hasson . |
| 3,882,849 | 5/1975 | Jamshidi . |
| 3,946,741 | 3/1976 | Adair . |
| 3,994,287 | 11/1976 | Turp et al. . |
| 4,013,080 | 3/1977 | Froning . |
| 4,018,228 | 4/1977 | Goosen . |
| 4,177,814 | 12/1979 | Knepshield et al. . |
| 4,210,146 | 7/1980 | Banko . |
| 4,220,155 | 9/1980 | Kimberling et al. . |
| 4,243,034 | 1/1981 | Brandt . |
| 4,254,762 | 3/1991 | Yoon . |
| 4,256,119 | 3/1981 | Gauthier . |
| 4,299,230 | 11/1981 | Kubota . |
| 4,356,826 | 11/1982 | Kubota . |
| 4,375,815 | 3/1983 | Burns . |
| 4,393,587 | 7/1983 | Kloosterman . |
| 4,411,653 | 10/1983 | Razi . |
| 4,414,974 | 11/1983 | Dotson et al. . |
| 4,499,898 | 2/1985 | Knepshield et al. . |
| 4,535,773 | 8/1985 | Yoon . |
| 4,556,059 | 12/1985 | Adamson, Jr. . |
| 4,559,041 | 12/1985 | Razi . |
| 4,601,710 | 7/1986 | Moll . |
| 4,637,393 | 1/1987 | Ray . |
| 4,654,030 | 3/1987 | Moll et al. . |
| 4,723,545 | 2/1988 | Nixon et al. . |

(List continued on next page.)

FOREIGN PATENT DOCUMENTS

| | | |
|---|---|---|
| 0350291 | 1/1990 | European Pat. Off. . |
| 836392 | 4/1952 | Fed. Rep. of Germany . |
| 344853 | 6/1968 | U.S.S.R. . |
| 537677 | 6/1975 | U.S.S.R. . |
| 921554 | 4/1982 | U.S.S.R. . |

OTHER PUBLICATIONS

"A Modified Instrument and Method for Laparoscopy"; Communications in brief, 1971, 886–887.
Ethicon, Inc. ENDOPATH TM Published Brochure, 1992.
"Needle for the Puncture and Lavage of the Abdominal Cavity"; Surgery; F. S. Subairov, 1976, 79–80.

*Primary Examiner*—Stephen C. Pellegrino
*Assistant Examiner*—William W. Lewis

[57] ABSTRACT

An apparatus is disclosed for automatically locking an obturator housing to a cannula housing of a trocar assembly when the obturator is advanced to a predetermined distal position. Two latch devices are mounted for pivotal movement within the obturator housing with each having at least one latch positioned at one end thereof. The pivoting latch devices are automatically pivoted into locked engagement with partial apertures or indentations in the cannula housing such that the obturator housing is secured to the cannula housing. Biasing springs are provided to automatically pivot the pivoting latch devices out of engagement with the cannula housing when the obturator is withdrawn to its proximal position.

15 Claims, 5 Drawing Sheets

U.S. PATENT DOCUMENTS

| | | |
|---|---|---|
| 4,730,613 | 3/1988 | Gordy . |
| 4,733,662 | 3/1988 | DeSatnick et al. . |
| 4,747,831 | 5/1988 | Kulli . |
| 4,813,940 | 3/1989 | Parry . |
| 4,817,631 | 4/1989 | Schnepp-Pesch et al. . |
| 4,902,280 | 2/1990 | Lander . |
| 4,931,042 | 6/1990 | Holmes et al. . |
| 4,943,280 | 7/1990 | Lander . |
| 5,002,557 | 3/1991 | Hasson . |
| 5,009,643 | 4/1991 | Reich et al. . |
| 5,030,206 | 7/1991 | Lander . |
| 5,066,288 | 11/1991 | Deniega et al. . |
| 5,104,382 | 4/1992 | Brinkerhoff et al. . |
| 5,114,407 | 5/1992 | Burbank . |
| 5,116,353 | 5/1992 | Green . |
| 5,122,122 | 6/1992 | Allgood . |
| 5,147,316 | 9/1992 | Castillenti . |
| 5,152,754 | 10/1992 | Plyley et al. . |
| 5,158,552 | 10/1992 | Borgia et al. . |

SAFETY TROCAR WITH LOCKING HANDLES

BACKGROUND OF THE INVENTION

1. Field of the Invention

This invention relates to locking handles for surgical trocar assemblies and more particularly to automatic locking handles which lock the handles prior to insertion into body tissue and which automatically releases the lock when the trocar assembly is inserted into the body tissue.

2. Description of the Prior Art

In endoscopic surgical procedures, surgery is performed in any hollow viscus of the body through narrow endoscopic tubes (or cannula) inserted through small entrance wounds in the skin. Similarly, in laparoscopic surgical procedures, surgery is performed in the interior of the abdomen through a small incision. In order to perform these procedures, a trocar assembly is utilized to facilitate the insertion of cannulas into the body. Trocars are sharp pointed surgical instruments used to puncture a body cavity which are generally adapted to be used together with the cannula. Once the body cavity has been punctured by the trocar, the trocar is removed from the cannula, thereby leaving the cannula extending into the body cavity. Endoscopic or laparoscopic surgical procedures are then performed through the cannula with accessory instrumentation such as laparoscopes, dissectors, graspers, and the like.

One type of commercially available safety trocar assembly, includes a spring-biased safety shield which is adapted to cover the trocar tip once the body cavity has been entered so as to provide an increased level of protection to internal structures from puncture or laceration. For example, U.S. Pat. No. 4,601,710 to Moll describes one type of trocar assembly which consists of two subassemblies: an obturator (or trocar) subassembly which includes an obturator tip (or sharp-tipped trocar) and a spring-loaded tubular safety shield positioned therearound, and a cannula subassembly. When ready for use, the obturator subassembly is inserted through the cannula subassembly. With the safety shield initially in its distal-most position covering the obturator tip, pressure is exerted against the skin with the trocar assembly causing the shield to be pushed rearwardly against the spring to expose the piercing tip of the trocar assembly. The tip penetrates the skin and underlying tissue with continued pressure. Once the tip has penetrated through the wall and has entered the cavity, the force against the front end of the shield ceases and the shield is automatically moved back to its distally extended position. Viscera and other internal tissue are thus protected from contact with the sharp piercing tip and potential damage therefrom.

U.S. Pat. No. 5,116,353 to Green (commonly assigned) describes another type of safety trocar assembly which includes an obturator subassembly having an automatically retracting obturator tip and a cannula subassembly. In operation, the obturator subassembly is inserted through the cannula subassembly and the sharp tip of the obturator subassembly is extended to its distal-most position. Exertion of pressure against the body wall will cause the sharp tip trocar to penetrate the body wall. Once the sharp tip penetrates the body wall, the counterforce against the sharp tip will cease causing the sharp tip to automatically retract into the cannula subassembly. Viscera and other internal tissue are thus protected from contact with the sharp piercing tip and potential damage therefrom.

When using the safety trocar assembly described in Green Pat. No. 5,116,353, if the surgeon inserts the trocar assembly through the body tissue in a manner that does not maintain the obturator subassembly in close approximation to the cannula subassembly when pressure is applied to the trocar assembly, the obturator subassembly may slide proximally, allowing the sharp tip to move away from the tissue.

Accordingly, it would be desirable to assist the surgeon in such procedures by providing a trocar assembly which automatically locks the obturator subassembly to the cannula subassembly before the surgeon inserts the trocar assembly into the body tissue.

SUMMARY OF THE INVENTION

The present invention relates to an apparatus for automatically locking an obturator housing in position with respect to a cannula housing associated therewith, the obturator housing having an obturator shaft having a cutting tip at the distal portion thereof and the cannula housing being adapted for reception of the obturator shaft. The apparatus comprises means positioned within the obturator housing and movable between a first position which permits relative movement thereof with respect to the cannula housing, and a second position which secures the obturator housing in position with respect to the cannula housing, means for automatically moving the obturator housing securing means from the first position to the second position when the obturator shaft is advanced to a predetermined distal position with respect to the cannula housing, and means for automatically moving the obturator housing securing means to the first position when the obturator shaft moves proximally from the predetermined distal position.

In another embodiment the apparatus for automatically locking an obturator housing to a cannula housing of a trocar assembly comprises pivoting means positioned within the obturator housing having at least one latch for securing the obturator housing to the cannula housing, means for automatically moving the pivoting means into engagement with the cannula housing when the obturator is advanced distally, and means positioned within the cannula housing for receiving the at least one latch. Biasing means is also provided which is operatively connected to the pivoting means for biasing the pivoting means out of engagement with the cannula housing. The pivoting means preferably comprises at least one pin extending substantially perpendicular to the longitudinal axis of the obturator housing. Also, the at least one latch preferably comprises a portion extending in a direction generally transverse to the longitudinal axis of the obturator housing and adapted for engaged reception by the receiving means of the cannula housing.

The pivoting means preferably comprises at least two latch members pivotally mounted within the obturator housing and adapted for movement between first positions which permit relative longitudinal movement between the obturator housing and the cannula housing and second positions which secure the relative longitudinal positions thereof.

A trocar assembly is also disclosed which comprises a cannula assembly having a cannula housing; an obturator housing; an obturator sleeve secured to the obturator housing and extending distally therefrom; an obturator shaft positioned in coaxial alignment with the obturator sleeve and having a proximal end operatively connected to the obturator housing; and a cutting tip positioned at the distal end of the obturator shaft. The trocar assembly also includes releasable locking means associated with the obturator shaft for releasably maintaining the obturator tip in a predetermined distal position, biasing means for retracting the obturator tip from the distal position to a predetermined proximal position in response to release of the releasable locking means, and securing means associated with the obturator housing for automatically securing the obturator housing longitudinally with respect to the cannula housing when the obturator tip is advanced to the predetermined distal position and for automatically unlocking the securing means when the obturator tip is retracted.

The securing means preferably comprises pivoting means positioned within the obturator housing having at least one latch positioned at the distal end thereof for securing the obturator housing to the cannula housing, means for automatically moving the pivoting means into engagement with the cannula housing when the obturator is advanced distally, means positioned within the cannula housing for receiving the at least one latch, and biasing means operatively connected to the pivoting means for biasing the pivoting means out of engagement with the cannula housing.

In a preferred embodiment, the pivoting means further comprises a curved body having at least one pin connected to a proximal end thereof, such that the at least one pin extends substantially perpendicular to the longitudinal axis of the obturator housing. The latch comprises a curved member having a first end positioned at a distal end of the curved body and a second end positioned towards a proximal end of the obturator housing.

A method is also disclosed for inserting a trocar assembly into body tissue, the trocar assembly having an obturator housing having an obturator shaft and cutting tip extending distally therefrom and positioned within an obturator sleeve, and a cannula housing having a cannula extending distally therefrom, the cannula housing adapted to receive the obturator assembly substantially in longitudinal coaxial alignment therewith, comprising advancing the obturator shaft and the cutting tip to expose the cutting tip from the cannula, such that the cutting tip is maintained in the exposed position, automatically latching the obturator housing to the cannula housing in response to advancement of the obturator tip to the exposed position, advancing the obturator tip against the body tissue such that the body tissue exerts a counterforce against the obturator tip, and automatically releasing the obturator housing from the cannula housing in response to proximal movement of the obturator tip from the advanced position upon removal of the counterforce therefrom.

BRIEF DESCRIPTION OF THE DRAWINGS

Preferred embodiments of the invention are described hereinbelow with reference to the drawings wherein.

DETAILED DESCRIPTION OF THE INVENTION

Figure 1:
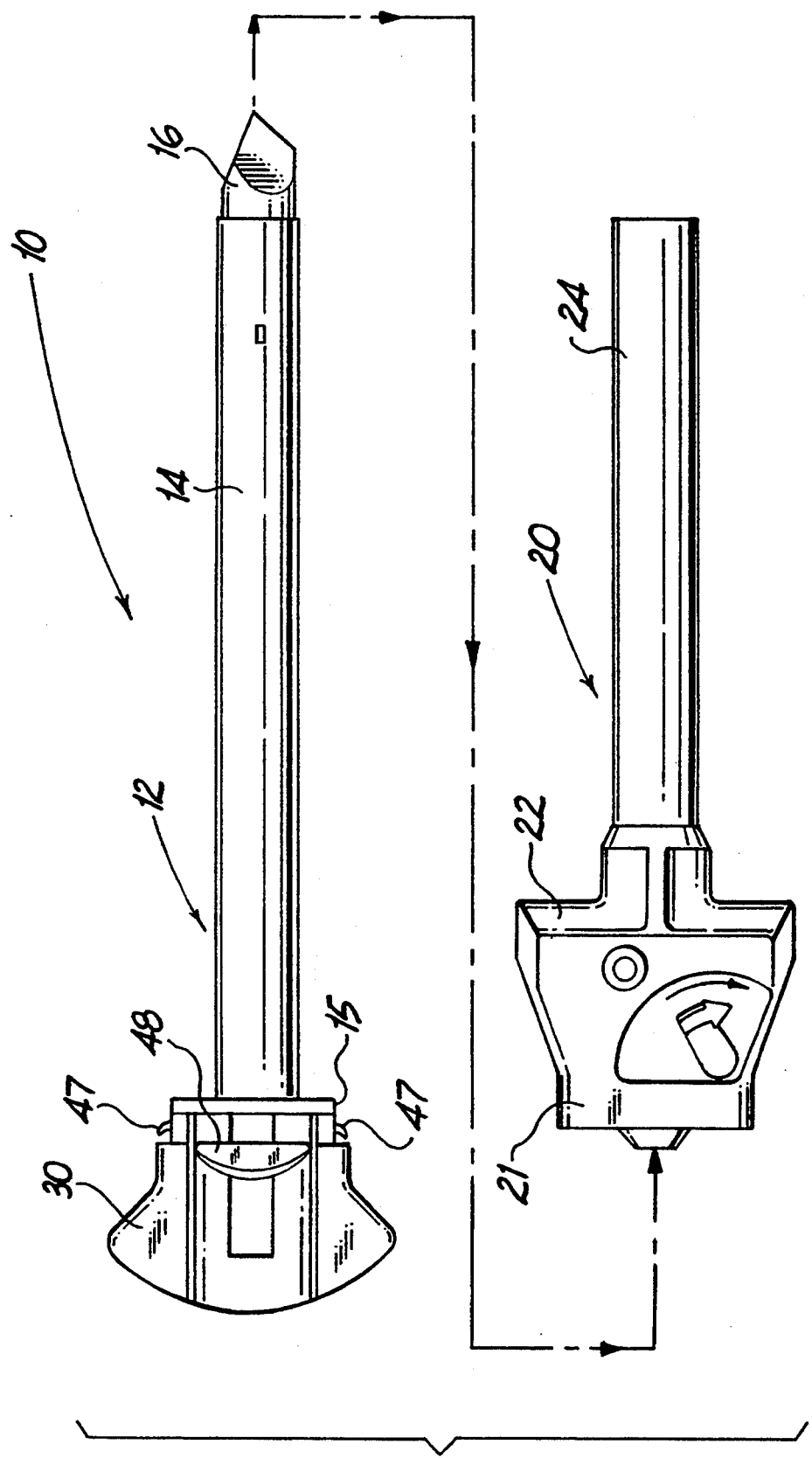
FIG. 1 is a plan view with parts separated, of a preferred trocar assembly of the present invention, illustrating an obturator subassembly and cannula subassembly.

Referring to FIG. 1, the preferred trocar assembly 10 is shown in an unassembled condition with obturator subassembly 12 separated from cannula subassembly 20. Generally, obturator subassembly 12 includes obturator housing 30 capable of being releasably secured to cannula housing 22 of cannula subassembly 20, obturator sleeve 14 and obturator tip 16. Extending outwardly from the distal end 15 of obturator housing 30 are two latches 47 associated with the latching system of the present invention. Latches 47 are configured to engage corresponding slots in the proximal end of cannula housing 22, thereby securing the two housings together.

Figure 2:
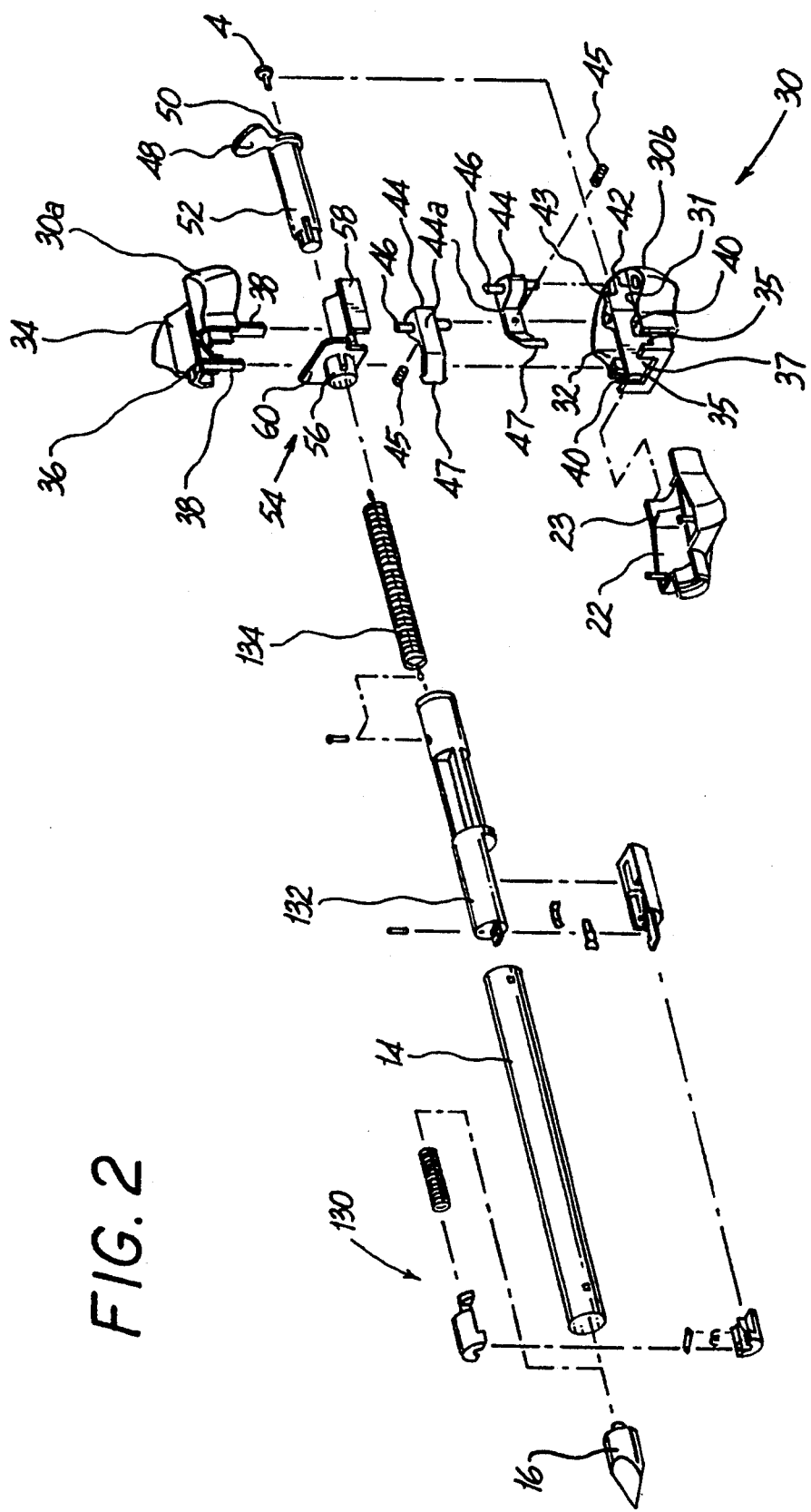
FIG. 2 is an exploded view of the obturator subassembly of FIG. 1, illustrating pivot arms having catches positioned at one end thereof.

Preferably, as shown in FIG. 2, obturator housing 30 includes upper housing 30a and lower housing 30b which are suitably attached by ultrasonic welding, adhesives, or the like. Upper housing 30a includes two mounting legs 38 which are adapted to fit within corresponding apertures 40 in lower housing 30b. Upper housing 30a and lower housing 30b also include apertures 42 which are aligned to engage corresponding pivot pins 46 on pivot arms 44. Guide track 34 in upper housing 30a has a generally semi-circular shape and is provided with slot 36 to receive and somewhat conceal button 48 so that when a surgeon grasps the obturator housing 30, movement of button 48 distally and proximally along slot 36 is permitted.

Figure 3:
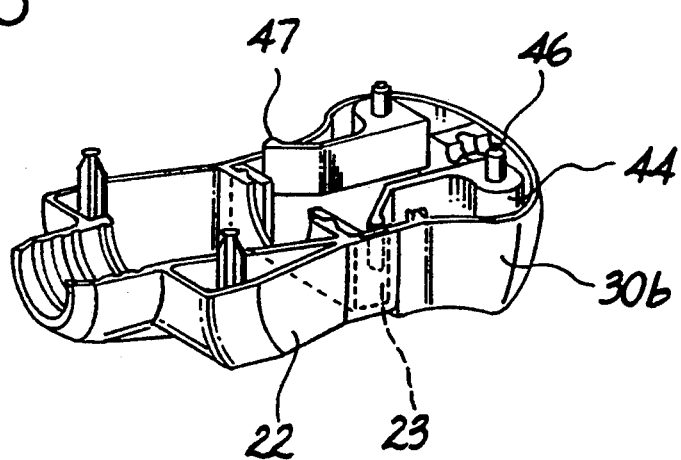
FIG. 3 is a perspective view of the inner portion of one half section of the obturator housing and the cannula housing of FIG. 1, illustrating the pivotal latch system for attaching the cannula housing to the obturator housing.

The latching system of the present invention is best shown in FIGS. 2 and 3. Within obturator housing 30 are pivot arms 44 having pivot pins 46 positioned at the proximal end thereof, and latches 47 positioned at the distal end thereof. Pivot arms 44 are configured to pivot within obturator housing 30, such that when pivoted toward respective side walls 31 or 32 latches 47 extend beyond the obturator housing through openings 35. Pivot arms 44 may be fabricated from materials such as plastic, metals or any other known material which can form a rigid structure sufficient to lock the obturator housing to the cannula housing. For example, pivot arms 44 may be constructed from a plastic material formed as a substantially "C" shaped body, with the distal end of the "C" shaped body formed as a hook-like or partially "U" shaped member as shown. The hook-like shape is provided for engaging a corresponding slot within the cannula housing. The proximal end of the "C" shaped body has a pair of pins 46 extending perpendicular to the longitudinal axis of the cannula to allow the body to pivot within obturator housing 30.

Referring again to FIG. 2, biasing springs 45 are positioned to engage pivot arms 44 and associated side walls 31 and 32 within obturator housing 30. In the normal position, pivot arms 44 are biased towards the center opening of obturator housing 30 so that latches 47 are retained within the housing. Distal movement of button 48 causes slide tube 52 to cam against the interior surfaces 44a of pivot arms 44 to cause pivot arms 44 to pivot in a direction traverse to the motion of the slide tube 52. This movement causes latches 47 to extend beyond the distal portion of obturator housing 30 through openings 35, as shown in FIGS. 1 and 3.

As shown in FIG. 2, tube guide 54 is coaxially aligned with slide tube 52 to allow longitudinal movement of slide tube 52 within cannula housing 30. Button ring 50 is secured to the proximal end of slide tube 52 to attach button 48 so as to extend beyond the upper surface of obturator housing 30a and to slide within channel 36. Tube guide 54 is configured to be positioned within center opening 37 of obturator housing 30, as shown in FIG. 2. Tube guide 54 includes tubular flange 56 positioned at the distal end thereof for securing the proximal end of obturator sleeve 14 to obturator housing 30. Track 58 is also provided to guide slide tube 52 in coaxial alignment with flange 56, and plate 60 is positioned between flange 56 and track 58 to form, at least partially, the distal face of obturator housing 30.

Tension spring 134 extends through flange 56 and slide tube 52 and is connected at a proximal end to pin 49 which is positioned to engage notch 43 in cannula housing 30. The distal end of tension spring 134 and the distal end of slide tube 52 are connected to the proximal end of obturator shaft 132. The distal end of obturator shaft 132 is operatively connected to the proximal end of releasing system 130 and the distal end of releasing system 130 is connected to the proximal end of obturator tip 16. When the releasing system is activated, tension spring 134 automatically causes proximal movement of obturator tip 16, obturator shaft 132 and slide tube 52.

Figure 4:
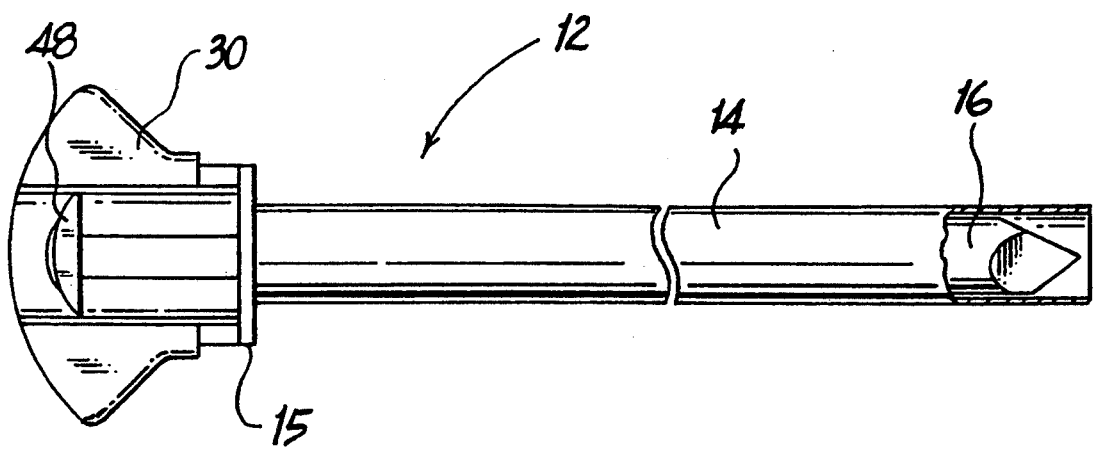
FIG. 4 is a plan view, partially cut away, of the obturator subassembly of FIG. 1, illustrating the obturator tip in a retracted position.

Preferably, releasing system 130 provides automatic locking of obturator tip 16 in its distal-most position, shown in FIG. 1, and automatic releasing of obturator tip 16 to its proximal most position, shown in FIG. 4. Suitable releasing systems and their operation are disclosed in commonly assigned U.S. Pat. No. 5,116,353 to Green and U.S. Patent Application Ser. No. 632,085 to Guy et at., filed Dec. 21, 1990, both of which are incorporated herein by reference.

Figure 5:
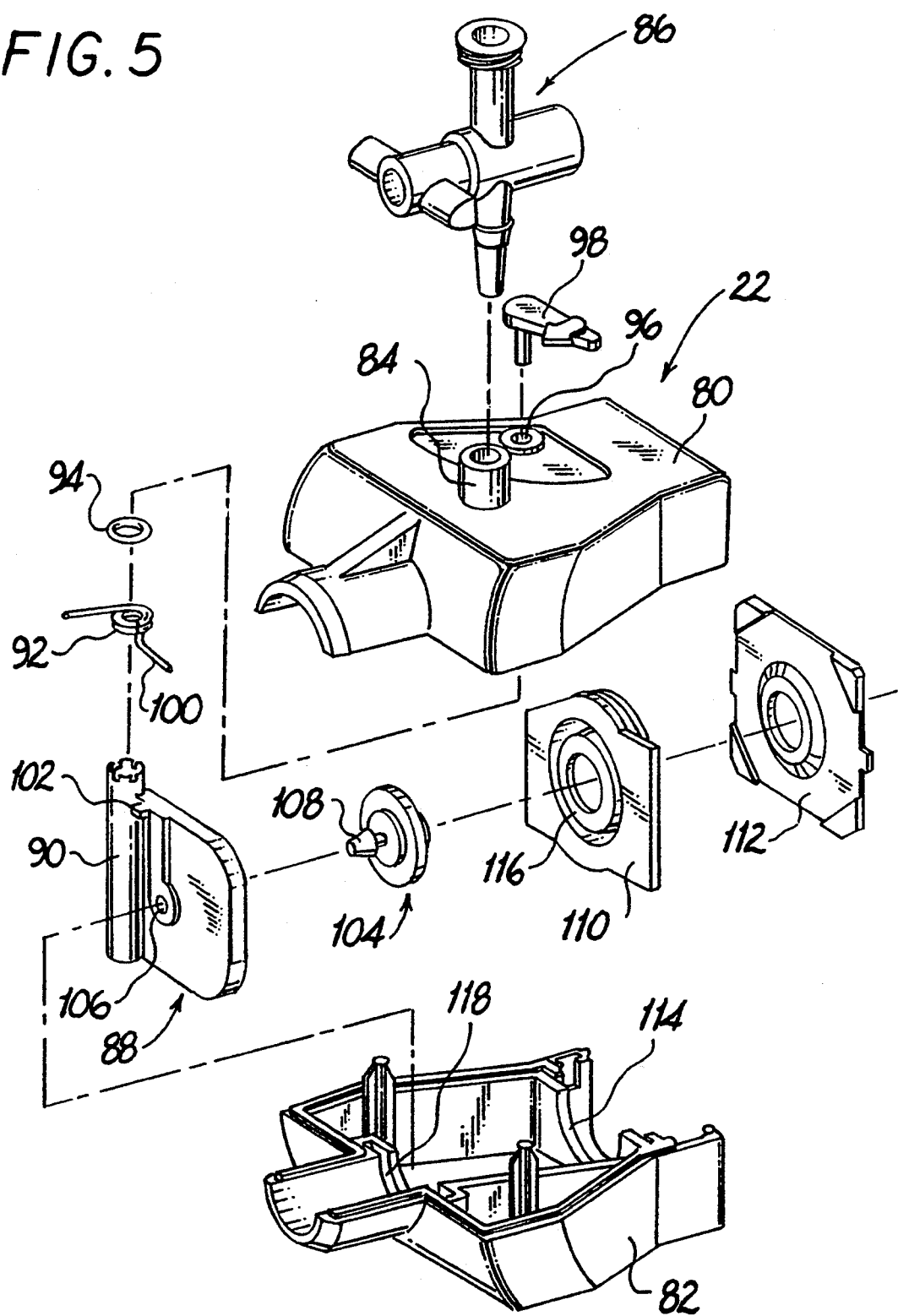
FIG. 5 is a perspective view with parts separated of the cannula housing of the cannula subassembly of FIG. 1.

Turning to FIG. 5, cannula housing 22 generally includes upper cannula housing section 80 and lower cannula housing section 82. A tubular port 84 is formed on upper cannula housing section 80 and receives stopcock assembly 86. Valve support body 88 is pivotally mounted within cannula housing 22 with the lower end of support leg 90 seating into lower cannula body 82 and the upper end passing through helically wound torsion spring 92, O-ring 94, aperture 96 in upper cannula body 80, and into cooperation with external lever 98. Transverse leg 100 of torsion spring 92 is positioned below lip 102 which extends from the upper portion of valve support body 88. Self-seating valve 104 mounts onto valve support body 88 through cooperation between aperture 106 in support body 88 and distally extending mounting rod 108 on valve 104. A seal member 110 and stabilizer plate 112 are mounted into cannula housing 22, e.g., with an adhesive, in cooperation with internal mating flanges 114 within upper and lower cannula housings 80 and 82. Seal member 110 includes a gasket 116 which forms a gas seal with valve 104 when valve support body 88 is pivoted into a substantially parallel relation with seal member 110. A second set of internal mating flanges 118 are provided toward the distal end of upper and lower cannula housings 80 and 82 to receive a flange formed at the proximal end of cannula 24.

Figure 6:
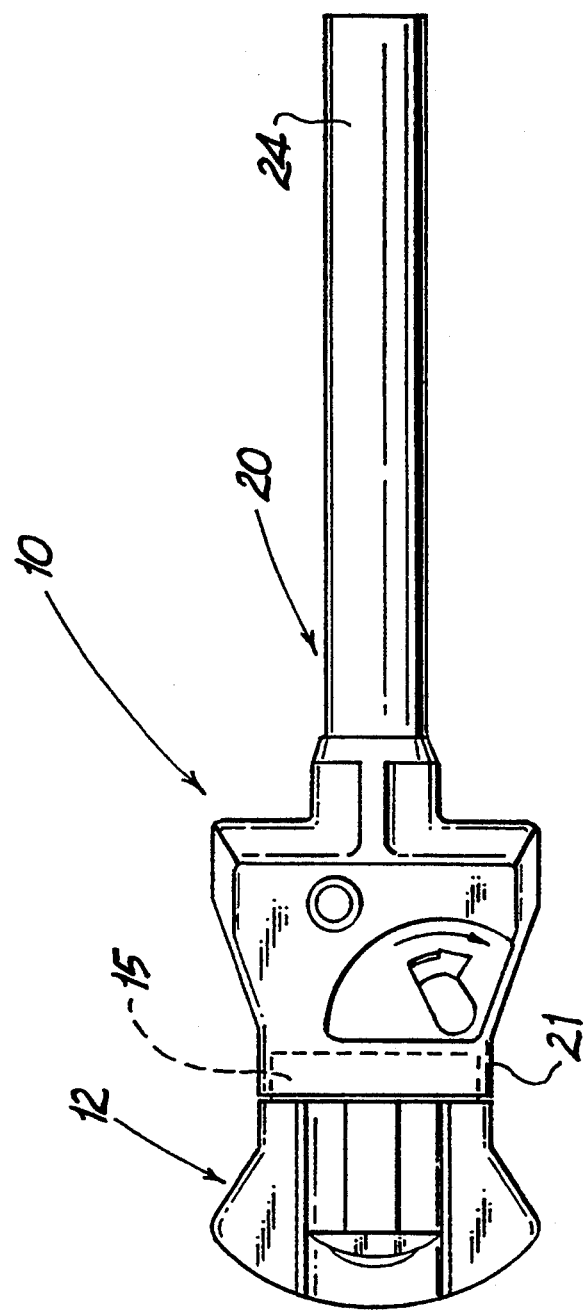
FIG. 6 is a plan view of the trocar assembly of FIG. 1, illustrating the obturator subassembly and cannula subassembly in an assembled condition, and with the obturator tip in a retracted position.

In operation, obturator subassembly 12 is initially inserted into the proximal end of cannula subassembly 20 with obturator tip 16 in a retracted position (or its proximal-most position), as shown in FIG. 6. Contact with obturator sleeve 14 and/or obturator tip 16 pivots valve support body 88 so as to provide free passage for obturator sleeve 14 and obturator tip 16 into cannula 24. Alternatively, valve support body 88 may be manually pivoted using lever 98. As obturator sleeve 14 enters cannula housing 22, a gas seal is provided therewith by gasket 116. The surgeon continues to advance obturator sleeve 14 into cannula subassembly 20 until distal portion 15 of obturator housing 30 engages proximal portion 21 of cannula housing 22, as shown in FIG. 6.

With the obturator tip 16 of the obturator subassembly in its retracted position, button 48 is in its proximal-most position, as shown in FIG. 6. This allows springs 45 to bias pivot arms 44 towards the center of obturator housing 30 leaving latches 47 in a non-engaging position. When the surgeon is ready to use trocar assembly 10, button 48 is advanced distally within channel 36 of obturator housing 30. Sliding button 48 in a distal direction causes obturator tip 16 to extend beyond the obturator sleeve 14 and the cannula 24, shown in FIG. 1, and remain in the extended position. As noted above, distal movement of button 48 also causes latches 47 to automatically extend beyond distal portion 15 of obturator housing 30 and engage corresponding internal slots 23 within cannula housing 22, as shown in FIG. 3. Slots 23 are formed as partial indentations within the proximal side walls of cannula housing 22. The lower part of each slot is provided in lower cannula housing section 82 and the remaining portion of each slot 23 is provided by upper cannula housing section 80. Once secured to cannula subassembly 20, the obturator subassembly 12 remains fixed thereto until obturator tip 16 releases and automatically retracts into cannula 24 and obturator sleeve 14.

Once obturator tip 16 is extended, the surgeon advances trocar assembly 10 against the patient's body wall and this motion creates a counterforce against obturator tip 16. When obturator tip 16 passes through the body wall and enters the body cavity the counterforce ceases. The absence of counterforce allows the releasing system of the obturator subassembly to automatically activate and, as a result, obturator shaft 132, slide tube 52 and button 48 move proximally under the return force of tension spring 134. The proximal movement of slide tube 52 removes the camming action against pivot arms 44, thus enabling pivot arms 44 to automatically pivot towards the center opening of obturator housing 30, under a transverse expansive force from springs 45, and thereby to disengage from slots 23 within cannula housing 22. Trocar assembly 10 therefore assumes the initial position, shown in FIGS. 4 and 6, with obturator tip 16 within cannula 24 and obturator sleeve 14 and latches 47 disengaged from corresponding slots 23 within the proximal portion of the cannula subassembly.

Although the illustrative embodiments of the present invention have been described herein with reference to the accompanying drawings, it is to be understood that the invention is not limited to these precise embodiments, and that various other changes and modifications may be effected therein by one skilled in the art without departing from the scope or spirit of the invention. For example, a variety of cutting tip configurations may be employed with the trocar assembly of the invention, e.g., conical tips, dome tips, fluted tips, etc. Additional changes and modifications will be apparent to those of ordinary skill.

What is claimed is:

1. Apparatus for locking an obturator housing to a cannula housing, said obturator housing having an obturator shaft extending distally therefrom, which comprises:
   (a) pivoting means positioned at least partially within said obturator housing and having at least one latch associated therewith for securing said obturator housing to said cannula housing;
   (b) latch receiving means positioned at a proximal end of said cannula housing for receiving said at least one latch;
   (c) actuating means operatively connected to said obturator shaft for moving said pivoting means such that said at least one latch engages said latch receiving means when said obturator shaft is advanced distally relative to said cannula housing, said actuating means being movable with respect to said obturator housing, and being housed at least in part by and accessible through an outer surface of said obturator housing; and
   wherein said at least one latch of said pivoting means automatically disengages from said latch receiving means when said obturator shaft moves proximally with respect to said cannula housing.

2. The apparatus according to claim 1, further comprising at least one spring which biases said pivoting means into engagement with said latch receiving means.

3. The apparatus according to claim 1, wherein said pivoting means comprises at least one pin at the proximal end thereof and extending substantially perpendicular to the longitudinal axis of said obturator housing.

4. The apparatus according to claim 3, wherein said at least one latch comprises a portion extending in a direction generally transverse to the longitudinal axis of said obturator housing and adapted for engaged reception by said receiving means of said cannula housing.

5. The apparatus according to claim 4, wherein said pivoting means comprises at least two latch members pivotally mounted within said obturator housing and adapted for movement between first positions which permit relative longitudinal movement between said obturator housing and said cannula housing and second positions which secure the relative longitudinal positions thereof.

6. Apparatus for automatically locking an obturator housing in position with respect to a cannula housing associated therewith, said obturator housing having an obturator shaft extending distally therefrom, said obturator shaft having cutting tip at the distal position thereof and said cannula housing being adapted for reception of said obturator shaft, which comprises:
   (a) securing means positioned at least partially within said obturator housing said securing means being movable between a first position which permits relative movement of said obturator housing with respect to said cannula housing, and a second position which permits securing said obturator housing in position with respect to said cannula housing; and
   (b) actuating means operatively connected to said obturator shaft and movable with respect to said obturator housing, said actuating means being housed at least in part by and accessible through an outer surface of said obturator housing, for moving said securing means from said first position to said second position when said actuating means is actuated to advanced said obturator shaft to a predetermined distal position with respect to said cannula housing;
   wherein said securing means is automatically moved from said second position to said first position when said obturator shaft is moved proximally from said predetermined distal position.

7. A trocar assembly, which comprises:
   (a) a cannula assembly having a cannula housing;
   (b) an obturator housing;
   (c) an obturator sleeve secured to said obturator housing and extending distally therefrom;
   (d) an obturator shaft positioned in coaxial alignment with said obturator sleeve and having a proximal end operatively connected to said obturator housing and a cutting tip positioned at the distal end thereof;
   (e) releasable locking means at least partially secured to said obturator shaft for releasably maintaining said obturator tip in a predetermined distal position;
   (f) biasing means for retracting said obturator tip from said distal position to a predetermined proximal position in response to release of said releasable locking means;
   (g) securing means positioned at least partially within said obtruator housing for securing said obturator housing longitudinally with respect to said cannula housing when said obturator tip is advanced to said predetermined distal position; and
   (h) actuating means operatively connected to said obturator shaft and movable with respect to said obturator housing, said actuating means being housed by and accessible through an outer surface of said obturator housing, for actuating said securing means to secure said obturator housing with respect to said cannula housing;
   wherein said securing means is released when said obturator tip is retracted to a predtermined proximal position.

8. The trocar assembly according to claim 7, wherein said securing means comprises:
   (a) pivoting means positioned within said obturator housing and having at least one latch positioned at the distal end thereof for securing said obturator housing to said cannula housing; and
   (b) latch receiving means positioned at a proximal end of said cannula housing for receiving said at least one latch.

9. The trocar assembly according to claim 8 wherein said pivoting means further comprises a curved body having at least one pin connected to a proximal end thereof, such that said at least one pin extends substantially perpendicular to the longitudinal axis of said obturator housing.

10. The trocar assembly according to claim 8, wherein said at least one latch comprises a curved member having a first end positioned at a distal end of said curved body and a second end positioned towards a proximal end of the obturator housing.

11. A trocar assembly comprising:

(a) a cannula assembly having a cannula housing having at least two slots formed within a proximal end thereof;

(b) an obturator assembly having an obturator housing, an obturator sleeve secured to said obturator housing and extending distally therefrom, and an obturator shaft positioned in coaxial alignment with said obturator sleeve and having a proximal end operatively connected to said obturator housing and a distal end cooperatively engaged with an obturator tip;

(c) means secured to at least a portion of said obturator shaft to releasably maintain said obturator tip in an extended position;

(d) actuating means operatively connected to said obturator shaft and movable with respect to said obturator housing, said actuating means being housed by and accessible through a face of said obturator housing, for actuating securing means positioned at least partially within said obturator shaft for releasably securing said obturator assembly to said cannula assembly;

(e) means for releasing said releasable obturator maintaining means;

(f) first biasing means for retracting said obturator tip from said extended position to a retracted position in response to release of said releasable obturator means; and (g) second biasing means for automatically releasing said securing means in response to retraction of said obturator tip, such that said obturator assembly is released from said cannula assembly.

12. The trocar assembly according to claim 11, wherein said securing means comprises at least one pivot arm having at least one latch positioned at a distal end thereof, pivotally secured to said obturator housing such that said at least one catch engages said at least one slot formed within said proximal end of said cannula housing.

13. The trocar assembly according to claim 12, wherein said at least one pivot arm further comprises, a curved body having at least one pin connected to a proximal end thereof, such that said at least one pin extends substantially perpendicular to the longitudinal axis of said body.

14. The trocar assembly according to claim 13, wherein said second biasing means is secured to said at least one pivot arm and positioned to engage an inner wall of said obturator housing, such that said at least one pivot arm is biased toward the center of said obturator housing.

15. A method for inserting a trocar assembly into body tissue, said trocar assembly having an obturator housing having an obturator shaft and cutting tip extending distally therefrom and positioned within an obturator sleeve, and a cannula housing having a cannula extending distally therefrom, said cannula housing adapted to cooperate with said obturator assembly substantially in longitudinal coaxial alignment therewith, comprising:

(a) advancing said obturator shaft and said cutting tip to expose said cutting tip from said cannula, such that said cutting tip is maintained in said exposed position, by distally advancing an actuating means operatively connected to said obturator shaft, said actuating means being housed by and accessible through a face of said obturator housing;

(b) automatically latching said obturator housing to said cannula housing in response to advancement of said obturator tip to said exposed position;

(c) advancing said obturator tip against the body tissue such that the body tissue exerts a counterforce against said obturator tip; and (d) automatically releasing said obturator housing from said cannula housing in response to proximal movement of said obturator tip from said advanced position upon removal of said counterforce therefrom.

* * * * *